US010267728B2

(12) United States Patent
Yang et al.

(10) Patent No.: US 10,267,728 B2
(45) Date of Patent: Apr. 23, 2019

(54) SYSTEMS AND METHODS FOR DETECTING OXYGEN IN-SITU IN A SUBSTRATE AREA OF A SUBSTRATE PROCESSING SYSTEM (71) Applicant: Lam Research Corporation, Fremont, CA (US)

(72) Inventors: Dengliang Yang, Union City, CA (US); Ilia Kalinovski, Berkeley, CA (US); Haoquan Fang, Sunnyvale, CA (US); David Cheung, Foster City, CA (US)

(73) Assignee: LAM RESEARCH CORPORATION, Fremont, CA (US)

( * ) Notice: Subject to any disclaimer, the term of this patent is extended or adjusted under 35 U.S.C. 154(b) by 35 days.

(21) Appl. No.: 15/701,796

(22) Filed: Sep. 12, 2017

(65) Prior Publication Data
US 2018/0088031 A1    Mar. 29, 2018

Related U.S. Application Data (60) Provisional application No. 62/400,860, filed on Sep. 28, 2016.

(51) Int. Cl.
*G01N 21/27* (2006.01)
*G01J 3/443* (2006.01)
(Continued)

(52) U.S. Cl.
CPC .............. *G01N 21/27* (2013.01); *G01J 3/443* (2013.01); *G01N 21/62* (2013.01); *G01N 21/68* (2013.01);
(Continued)

(58) Field of Classification Search
CPC ... G01J 3/443; G01N 2021/625; G01N 21/27; G01N 21/62; G01N 21/68; G01N 2201/061
See application file for complete search history.

(56) References Cited

U.S. PATENT DOCUMENTS 7,270,724 B2 * 9/2007 Elliott ..................... C23C 16/50
                                                        118/50.1
7,932,181 B2 * 4/2011 Singh ..................... H01J 37/321
                                                        216/67
(Continued)

OTHER PUBLICATIONS

"Actinometry of O, N and F atoms" Inventors: D V Lopaev et al. Published Jan. 23, 2017, © 2017 IOP Publishing Ltd Journal of Physics D: Applied Physics, vol. 50, No. 7, 1 page.
(Continued)

*Primary Examiner* — David P Porta
*Assistant Examiner* — Faye Boosalis (57) ABSTRACT A measurement system to measure a concentration of neutral gas species above a substrate includes a substrate support located in a chamber to support a substrate. A plasma source generates plasma in the chamber above the substrate. The plasma generates metastable species having higher ionization energy than a neutral gas species. The metastable species excite the neutral gas species located above the substrate. An optical emission spectrometer (OES) sensor measures spectra from a location above the substrate while the plasma is generated by the plasma source. A controller is configured to determine a concentration of the neutral gas species in a region above the substrate based on the measured spectra and to selectively process the substrate based on the concentration.

28 Claims, 7 Drawing Sheets (51) Int. Cl.
*G01N 21/62* (2006.01)
*G01N 21/68* (2006.01)

(52) U.S. Cl.
CPC . *G01N 2021/625* (2013.01); *G01N 2201/061* (2013.01)

(56) References Cited

U.S. PATENT DOCUMENTS

| | | | | |
|---|---|---|---|---|
| 2008/0090022 | A1* | 4/2008 | Ovshinsky | C23C 16/24 427/569 |
| 2015/0214067 | A1* | 7/2015 | Zhang | H01J 37/32422 438/724 |
| 2017/0032982 | A1 | 2/2017 | Drewery et al. | |
| 2017/0200586 | A1* | 7/2017 | Treadwell | H01J 37/32082 |
| 2018/0088031 | A1* | 3/2018 | Yang | G01N 21/27 |

OTHER PUBLICATIONS

U.S. Appl. No. 62/275,837, filed Jan. 7, 2016, Jason Lee Treadwell et al.

\* cited by examiner

SYSTEMS AND METHODS FOR DETECTING OXYGEN IN-SITU IN A SUBSTRATE AREA OF A SUBSTRATE PROCESSING SYSTEM

CROSS-REFERENCE TO RELATED APPLICATIONS

This application claims the benefit of U.S. Provisional Application No. 62/400,860, filed on Sep. 28, 2016. The entire disclosure of the application referenced above is incorporated herein by reference.

FIELD

The present disclosure relates to substrate processing systems, and more particularly to systems and methods for detecting molecular oxygen in-situ in a substrate processing system.

BACKGROUND

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Substrate processing systems may be used to etch film on a substrate such as a semiconductor wafer. The substrate processing systems typically include a processing chamber, a gas distribution device, and a substrate support. During processing, the substrate is arranged on the substrate support. Different gas mixtures may be introduced into the processing chamber. Radio frequency (RF) plasma may be used to activate chemical reactions.

In some situations, it is important to detect trace levels of molecular oxygen ($O_2$) in the vicinity of an upper surface of the substrate. For example, some photoresist strip or surface modification processes are very sensitive to oxidation of underlying films. Current approaches for measuring trace levels of molecular oxygen in a vacuum chamber typically use a residual gas analyzer (RGA). The operation of the RGA is accomplished using an open ion source (OIS) or a closed-ion-source (CIS) that ionizes gas and detects mass based on quadrupole spectroscopy. RGA typically has a sensitivity that is less than 1 part per million (ppm). OIS detection systems are directly mounted to the processing chamber and have a maximum operating pressure of $10^{-4}$ Torr. CIS detection systems typically require a differential pumping system and therefore have reduced sensitivity. Furthermore, the sensitivity of the RGA decays over time due to gas corrosion (~1 year with a molecular hydrogen ($H_2$) process) and then costly replacement is required.

SUMMARY

A measurement system to measure a concentration of neutral gas species above a substrate includes a substrate support located in a chamber to support a substrate. A plasma source generates plasma in the chamber above the substrate. The plasma generates metastable species having higher ionization energy than a neutral gas species. The metastable species excite the neutral gas species located above the substrate. An optical emission spectrometer (OES) sensor measures spectra from a location above the substrate while the plasma is generated by the plasma source. A controller is configured to determine a concentration of the neutral gas species in a region above the substrate based on the measured spectra.

In other features, the controller is configured to selectively process the substrate based on the concentration.

In other features, the controller determines the concentration of the neutral gas species by comparing an intensity of the measured spectra at a predetermined wavelength to a predetermined reference. The controller determines the concentration of the neutral gas species using a lookup table that is indexed by an intensity of the measured spectra at a predetermined wavelength. The controller determines the concentration of the neutral gas species using a predetermined function and an intensity of the measured spectra at a predetermined wavelength.

In other features, the plasma source generates the plasma using a plasma gas mixture that does not include the neutral gas species. A plasma gas mixture is supplied to the plasma source includes helium. The metastable species includes helium metastable species.

In other features, the plasma gas mixture further includes at least one gas selected from a group consisting of argon, neon and molecular nitrogen. The neutral gas species includes molecular oxygen. The neutral gas species includes molecular nitrogen. The OES sensor measures spectra travelling parallel to a plane including the substrate. The chamber includes a viewport. A collimator tube is arranged between the viewport and the OES sensor to collimate the spectra. The collimator tube has an aspect ratio that is greater than 5:1. The neutral gas species includes oxygen species, and the helium metastable species enhance characteristic emission spectra of the oxygen species at at least one of 777 nm and 844 nm.

A method for measuring a concentration of neutral gas species above a substrate includes arranging a substrate on a substrate support in a chamber; generating plasma in the chamber above the substrate. The plasma generates metastable species having higher ionization energy than a neutral gas species. The metastable species excites the neutral gas species located above the substrate. The method includes measuring spectra from a location above the substrate using an optical emission spectrometer (OES) sensor while the plasma is present; and determining a concentration of the neutral gas species in a region above the substrate based on the measured spectra.

In other features, the method further includes selectively processing the substrate based on the concentration.

In other features, determining the concentration of the neutral gas species includes comparing an intensity of the measured spectra at a predetermined wavelength to a predetermined reference. Determining the concentration of the neutral gas species includes using a lookup table that is indexed by an intensity of the measured spectra at a predetermined wavelength.

Determining the concentration of the neutral gas species includes using a predetermined function and an intensity of the measured spectra at a predetermined wavelength. The method includes supplying a plasma gas mixture that does not include the neutral gas species. The method includes supplying a plasma gas mixture including helium. The metastable species includes helium metastable species.

In other features, the plasma gas mixture further includes at least one gas selected from a group consisting of argon, neon and molecular nitrogen. The neutral gas species includes molecular oxygen. The neutral gas species includes molecular nitrogen. The method includes measuring spectra travelling parallel to a plane including the substrate.

In other features, the method includes providing a viewport and arranging a collimator tube between the viewport and the OES sensor to collimate the spectra that is received by the OES sensor. The collimator tube has an aspect ratio that is greater than or equal to 5:1.

In other features, the neutral gas species includes molecular oxygen species, and the helium metastable species enhance characteristic emission spectra of the oxygen species at at least one of 777 nm and 844 nm.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIGS. 3-4B are flowcharts illustrating examples of flowcharts for determining molecular oxygen levels in a substrate processing chamber;

In the drawings, reference numbers may be reused to identify similar and/or identical elements.

DETAILED DESCRIPTION

In some examples, the present disclosure relates to detection systems and methods for detecting trace levels of molecular oxygen ($O_2$) within a substrate processing system. More particularly, the detection systems and methods employ optical emission spectroscopy (OES) to determine the presence and/or concentration of residual molecular oxygen ($O_2$) in the vicinity of the substrate for an oxidation-sensitive process. In some examples, the oxidation-sensitive process can include a photoresist strip process or other oxygen sensitive process. The detection systems and methods can be used to qualify a substrate processing system prior to running a production process or as a step in the production process.

While $O_2$ can be measured in a vacuum chamber using a residual gas analyzer (RGA) or mass spectrometer, these devices are very expensive and do not necessarily measure the $O_2$ in the vicinity of the substrate surface. For example, at a chamber pressure used during resist strip processing (such as about 1 Torr), it is possible that the concentration of $O_2$ varies with location in the processing chamber. In other words, the concentration of $O_2$ may vary in a downstream region in a pumping exhaust line where the RGA is typically located. Therefore, the RGA measurement does not necessarily correspond to the level of $O_2$ near the substrate surface.

OES has been used to measure excited species in a vacuum chamber or in plasma and to determine an endpoint of a plasma etching step. However, the gas species of interest to be detected by the detection system are neutral molecules of $O_2$, which may not be excited above the processing substrate. Without exciting the $O_2$, there is no emitted optical radiation so the OES approach does not work directly with these process conditions.

The detection systems and methods strike He plasma in a plasma source. In some examples, one or more other non-oxygen containing gases such as argon (Ar), molecular nitrogen ($N_2$) or Neon (Ne) may also be supplied to the processing chamber. For example, these additional gases may be supplied to stabilize the He plasma or for other reasons.

The He plasma produces energetic and long-lived He metastable species having energy that is sufficiently high to excite or ionize $O_2$. The He metastable species readily pass through holes in the showerhead. In addition, the OES sensor is optimally arranged so that it only detects optical emission from gas species in a chamber volume above the substrate (between the showerhead and substrate). In some examples, a high aspect ratio collimating tube is arranged in front of the OES sensor to collimate the incident light such that only light travelling parallel to the substrate surface is detected.

The detection systems and methods use the OES sensor to detect highly sensitive background molecular oxygen ($O_2$) concentrations. The detection systems and methods are compatible with existing chamber designs that include optical viewports. In some examples, the detection systems and methods use helium (He) plasma to enhance the characteristic emission of O species, such as those found at emission wavelengths of 777 nm, 844 nm and/or other wavelengths. In some examples, the intensity of the emission lines is compared to a predetermined value and a subsequent process is performed if the intensity is less than the predetermined value.

Figure 7:
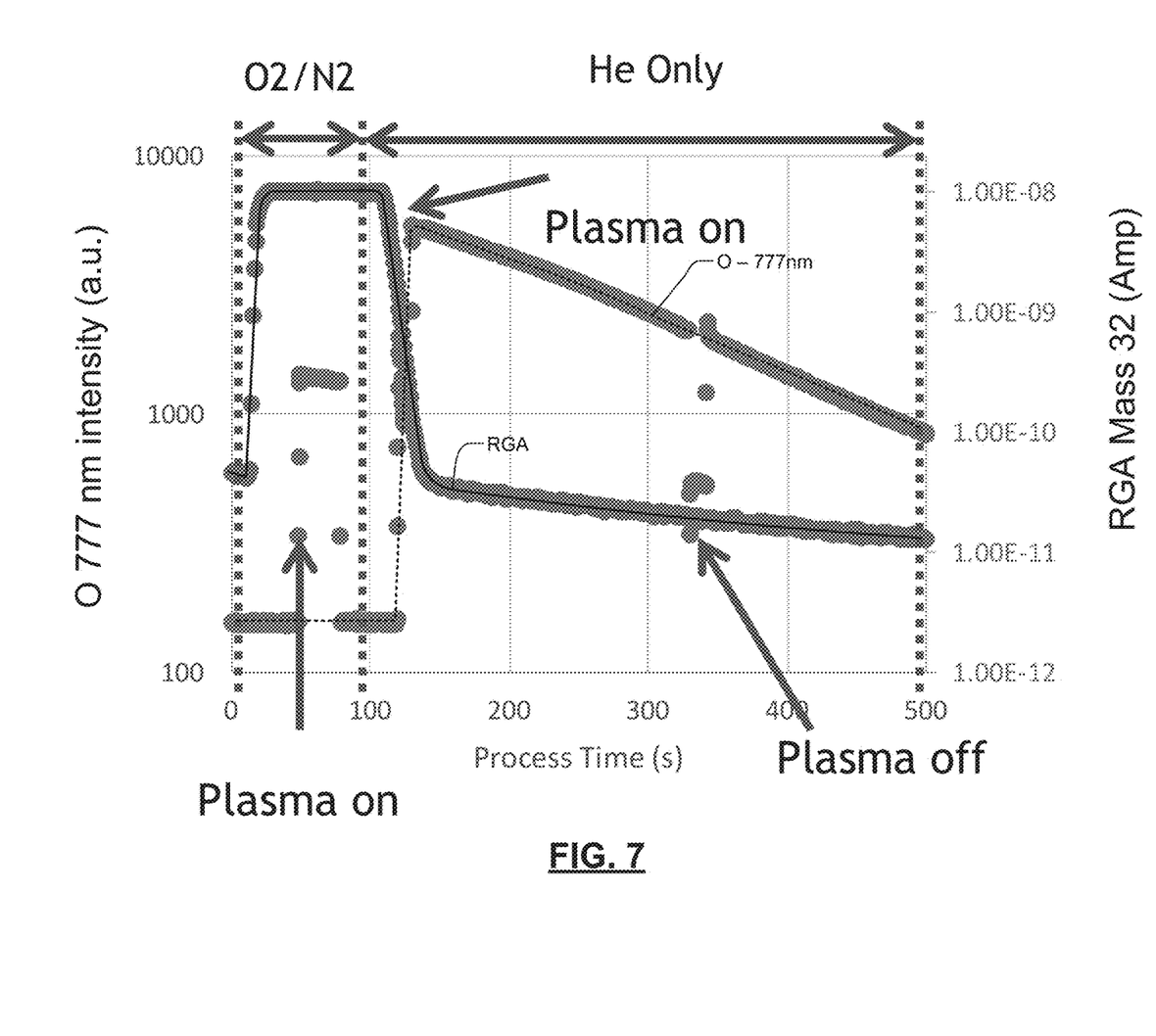
FIG. 7 is a graph illustrating an example of measured spectral intensity as a function of process time for OES and RGA.

In some examples, the concentration of the O species can also be quantitatively correlated to $O_2$ concentration. For certain gas species and pressure/power conditions, the concentration of the O species is approximately proportional to $O_2$ concentration. In some examples, the intensity of the emission lines is used as an index to access a calibrated lookup table that outputs $O_2$ concentration. An example showing a relationship between O species emission lines (output by an OES sensor) and $O_2$ concentration (output by an RGA sensor) is shown in FIG. 7. In other examples, the intensity of the emission lines are used as an input variable for a function that outputs $O_2$ concentration.

The detection systems and methods are highly sensitive to background concentrations of molecular oxygen $O_2$. The detection systems and methods are capable of detecting trace levels of molecular oxygen located above the substrate area using direct plasma or downstream plasma. The detection systems and methods perform in-situ detection without invasive detection probes. The detection systems and methods can be used for detection of chamber leaks and background oxygen from leaks or outgassing. The detection systems and methods also enable atomic level low oxidation plasma processing.

Figure 1:
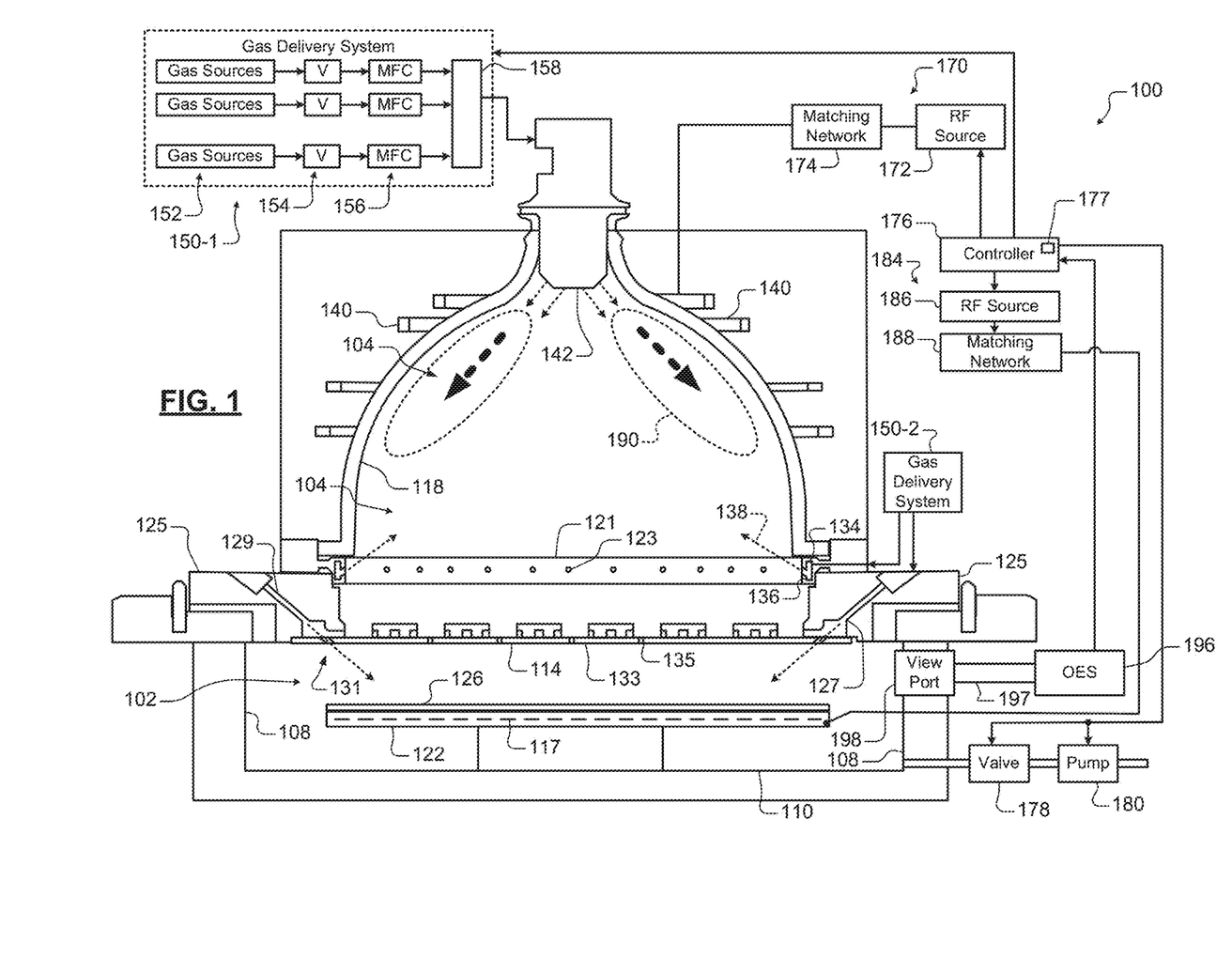
FIG. 1 is a functional block diagram of an example of a substrate processing system including a detection system according to the present disclosure.

The detection systems and methods may be used in substrate processing systems for photoresist stripping, ashing, physical vapor deposition (PVD), chemical vapor deposition (CVD), atomic layer deposition (ALD), etching or other substrate treatment steps. Referring now to FIG. 1, an example of a substrate processing chamber 100 is shown. While a specific substrate processing chamber is shown and described, the methods may be implemented using other types of substrate processing systems.

The substrate processing chamber 100 includes a lower chamber region 102 and an upper chamber region 104. The lower chamber region 102 is defined by chamber sidewall surfaces 108, a chamber bottom surface 110 and a lower surface of a gas distribution device 114.

The upper chamber region 104 is defined by an upper surface of the gas distribution device 114 and an inner surface of a dome 118. In some examples, the dome 118 rests on a first annular support 121. In some examples, the first annular support 121 includes one or more spaced holes 123 for delivering process gas to the upper chamber region 104. In some examples, the process gas is delivered by the one or more spaced holes 123 in an upward direction at an acute angle relative to a plane including the gas distribution device 114, although other angles/directions may be used. In some examples, a gas flow channel 134 in the first annular support 121 supplies gas to the one or more spaced holes 123.

The first annular support 121 may rest on a second annular support 125 that defines one or more spaced holes 127 for delivering process gas from a gas flow channel 129 to the lower chamber region 102. In some examples, holes 131 in the gas distribution device 114 align with the holes 127. In other examples, the gas distribution device 114 has a smaller diameter and the holes 131 are not needed. In some examples, the process gas is delivered by the one or more spaced holes 127 in a downward direction towards the substrate at an acute angle relative to the plane including the gas distribution device 114, although other angles/directions may be used.

In other examples, the upper chamber region 104 is cylindrical with a flat top surface and one or more flat inductive coils may be used. In still other examples, a single chamber may be used with a spacer located between a showerhead and the substrate support.

A substrate support 122 is arranged in the lower chamber region 102. In some examples, the substrate support 122 includes an electrostatic chuck (ESC), although other types of substrate supports can be used. A substrate 126 is arranged on an upper surface of the substrate support 122 during etching. In some examples, a temperature of the substrate 126 may be controlled by a heater plate 117, an optional cooling plate with fluid channels and one or more sensors (not shown); although any other suitable substrate support temperature control system may be used.

In some examples, the gas distribution device 114 includes a showerhead (for example, a plate 133 having a plurality of spaced holes 135). The plurality of spaced holes 135 extend from the upper surface of the plate 133 to the lower surface of the plate 133. In some examples, the spaced holes 135 have a diameter in a range from 0.1" to 0.75". In some examples, the showerhead is made of a conducting material such as aluminum or a non-conductive material such as ceramic with an embedded electrode made of a conducting material.

One or more inductive coils 140 are arranged around an outer portion of the dome 118. When energized, the one or more inductive coils 140 create an electromagnetic field inside of the dome 118. In some examples, an upper coil and a lower coil are used. A gas injector 142 injects one or more gas mixtures from a gas delivery system 150-1.

In some examples, a gas delivery system 150-1 includes one or more gas sources 152, one or more valves 154, one or more mass flow controllers (MFCs) 156, and a mixing manifold 158, although other types of gas delivery systems may be used. A gas splitter (not shown) may be used to vary flow rates of a gas mixture. Another gas delivery system 150-2 may be used to supply an etch gas or an etch gas mixture to the gas flow channels 129 and/or 134 (in addition to or instead of etch gas from the gas injector 142).

Suitable gas delivery systems are shown and described in commonly assigned U.S. patent application Ser. No. 14/945,680, entitled "Gas Delivery System" and filed on Dec. 4, 2015, which is hereby incorporated by reference in its entirety. Suitable single or dual gas injectors and other gas injection locations are shown and described in commonly assigned U.S. Provisional Patent Application Ser. No. 62/275,837, entitled "Substrate Processing System with Multiple Injection Points and Dual Injector" and filed on Jan. 7, 2016, which is hereby incorporated by reference in its entirety.

In some examples, the gas injector 142 includes a center injection location that directs gas in a downward direction and one or more side injection locations that inject gas at an angle with respect to the downward direction. In some examples, the gas delivery system 150-1 delivers a first portion of the gas mixture at a first flow rate to the center injection location and a second portion of the gas mixture at a second flow rate to the side injection location(s) of the gas injector 142. In other examples, different gas mixtures are delivered by the gas injector 142. In some examples, the gas delivery system 150-1 delivers tuning gas to the gas flow channels 129 and 134 and/or to other locations in the processing chamber as will be described below.

A plasma generator 170 may be used to generate RF power that is output to the one or more inductive coils 140. Plasma 190 is generated in the upper chamber region 104. In some examples, the plasma generator 170 includes an RF source 172 and a matching network 174. The matching network 174 matches an impedance of the RF source 172 to the impedance of the one or more inductive coils 140. In some examples, the gas distribution device 114 is connected to a reference potential such as ground. A valve 178 and a pump 180 may be used to control pressure inside of the lower and upper chamber regions 102, 104 and to evacuate reactants.

A controller 176 communicates with the gas delivery systems 150-1 and 150-2, the valve 178, the pump 180, and/or the plasma generator 170 to control flow of process gas, purge gas, RF plasma and chamber pressure. In some examples, plasma is sustained inside the dome 118 by the one or more inductive coils 140. One or more gas mixtures are introduced from a top portion of the chamber using the gas injector 142 (and/or holes 123) and plasma is confined within the dome 118 using the gas distribution device 114. In some examples, the controller 176 may include a lookup table 177 that is indexed by a line intensity value for the neutral gas species. For example only, the lookup table 177 may output $O_2$ concentration based on a line intensity value for O at 777 nm.

In some examples, an RF bias 184 is provided and includes an RF source 186 and an optional matching network 188. The RF bias power can be used to create plasma between the gas distribution device 114 and the substrate support or to create a self-bias on the substrate 126 to attract ions. The controller 176 may be used to control the RF bias power.

An optical emission spectrometer (OES) sensor 196 is connected to a viewport 198 or window into the lower chamber region 102 and to the controller 176 (or another computer (not shown)). In some examples, a collimating tube 197 may be arranged between the OES sensor 196 and the viewport 198 to collimate light. In some examples, the collimating tube 197 has a high aspect ratio. In other examples, the OES sensor 196 is attached directly adjacent to the viewport without a collimating tube. In some examples, the aspect ratio is greater than 5. In some examples, the aspect ratio is greater than 10. In some examples, the viewport 198 and the collimating tube 197 are arranged in a plane that is parallel to an area above a surface of the substrate 126.

Figure 2:
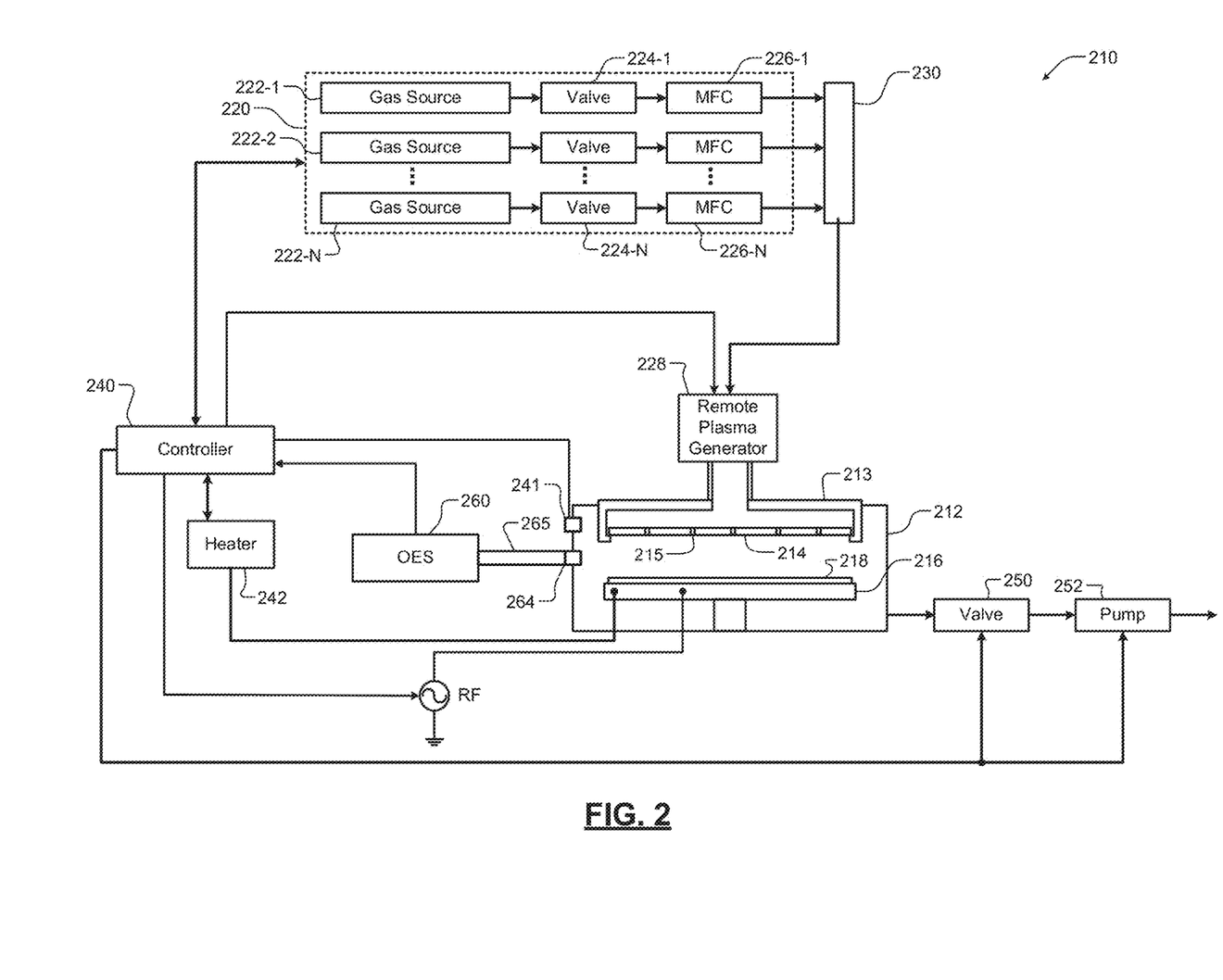
FIG. 2 is a functional block diagram of another example of a substrate processing system including a detection system according to the present disclosure.

Referring now to FIG. 2, an example of another substrate processing system 210 according to the present disclosure is shown. The substrate processing system 210 includes a processing chamber 212 and a gas distribution device 213 including a plate 214 or showerhead with spaced through holes 215. In some examples, remote plasma may be supplied to or created in the gas distribution device 213 as will be described further below. A substrate support 216 such as a pedestal or platen may be arranged in the processing chamber 212. During use, a substrate 218 such as a semiconductor substrate or other type of substrate may be arranged on the substrate support 216.

The substrate processing system 210 includes a gas delivery system 220. For example only, the gas delivery system 220 may include one or more gas sources 222-1, 222-2, . . . , and 222-N (collectively gas sources 222) where N is an integer greater than zero, valves 224-1, 224-2, . . . , and 224-N (collectively valves 224), and mass flow controllers (MFC) 226-1, 226-2, . . . , and 226-N (collectively MFC 226). Outputs of the gas delivery system 220 may be mixed in a manifold 230 and delivered to the remote plasma source and/or to the gas distribution device 213. The gas delivery system 220 supplies the plasma gas chemistry.

A controller 240 may be connected to one or more sensors 241 that monitor operating parameters in the processing chamber 212 such as temperature, pressure, etc. A heater 242 may be provided to heat the substrate support 216 and the substrate 218 as needed. A valve 250 and pump 252 may be provided to evacuate gas from the processing chamber 212.

For example only, a plasma generator 228 may be provided. In some examples, the plasma generator 228 is a downstream plasma source. The plasma generator 228 may include a plasma tube, an inductive coil or another device to create the remote plasma. For example only, the plasma generator 228 may use radio frequency (RF) or microwave power to create remote plasma using the gas chemistry identified above. In some examples, an inductive coil is wound around an upper stem portion of a showerhead and is excited by an RF signal generated by an RF source and a matching network. Reactive gas flowing through the stem portion is excited into a plasma state by the RF signal passing though the inductive coil. The controller 240 may be used to control the gas delivery system 220, the heater 242, the valve 250, the pump 252, and plasma generated by the remote plasma generator 228.

An OES sensor 260 is connected to a viewport 264 or window into the processing chamber 212 and to the controller 240 (or another computer (not shown)). In some examples, the viewport 264 is arranged parallel to a surface of the substrate 218. In some examples, a collimating tube 265 may be used. In some examples, the collimating tube 265 has a high aspect ratio. In other examples, the collimating tube is omitted. In some examples, the aspect ratio is greater than 5. In some examples, the aspect ratio is greater than 10. In some examples, the viewport 264 and the collimating tube 265 are arranged in a plane that is parallel to an area above a surface of the substrate 126.

The He plasma excitation generates high energy metastable species to enhance the characteristic emission from background $O_2$. The detection systems and methods can be used for in-situ detection without intrusive probes and is a highly sensitive detection approach. The detection systems and methods have a high dynamic range for $O_2$ detection over 6 decades. The components of the system have a long lifetime and are relatively easy to maintain.

In some examples using inductively coupled plasma, ICP power is set within a range between 500 W-5 kW, although other power levels may be used. In some examples, chamber pressure is set in a range between 20 mT and 10 T, although other chamber pressures can be used. In some examples, the flow rate for He is set in a range from 50 sccm to 20,000 sccm. In some examples, the plasma gas includes He. In some examples, the plasma gas includes He and one or more other carrier gases such as argon (Ar), molecular nitrogen ($N_2$) or molecular hydrogen ($H_2$).

Figure 3:
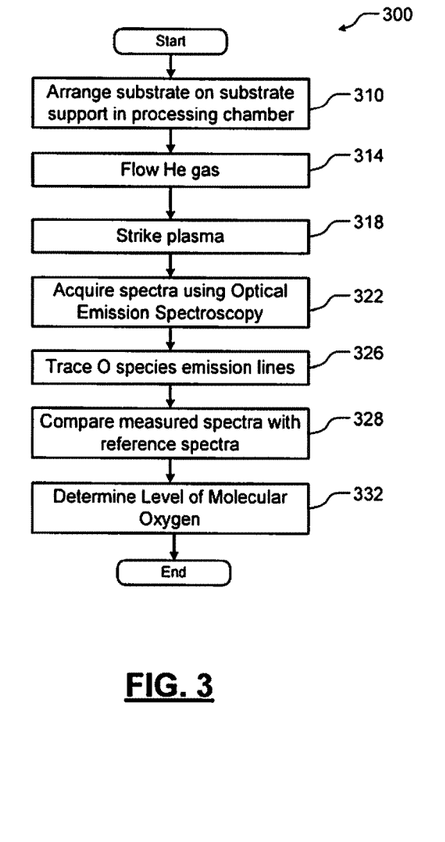

Referring now to FIG. 3, a method 300 for detecting molecular oxygen levels in an area above the substrate is shown. At 310, a substrate is arranged on a substrate support in the processing chamber. At 314, helium gas is supplied to the processing chamber. In some examples, additional gases such as carrier gases may be supplied along with the helium gas. At 318, plasma is struck in the processing chamber. At 322, measured spectra are acquired in the processing chamber using the OES sensor. At 326, the oxygen emission lines are traced and/or a magnitude is identified and tracked over time. At 328, emission line(s) of the measured spectra are compared with emission line(s) for reference spectra. At 332, a level of molecular oxygen in the chamber is determined based on the comparison.

Figure 4A:
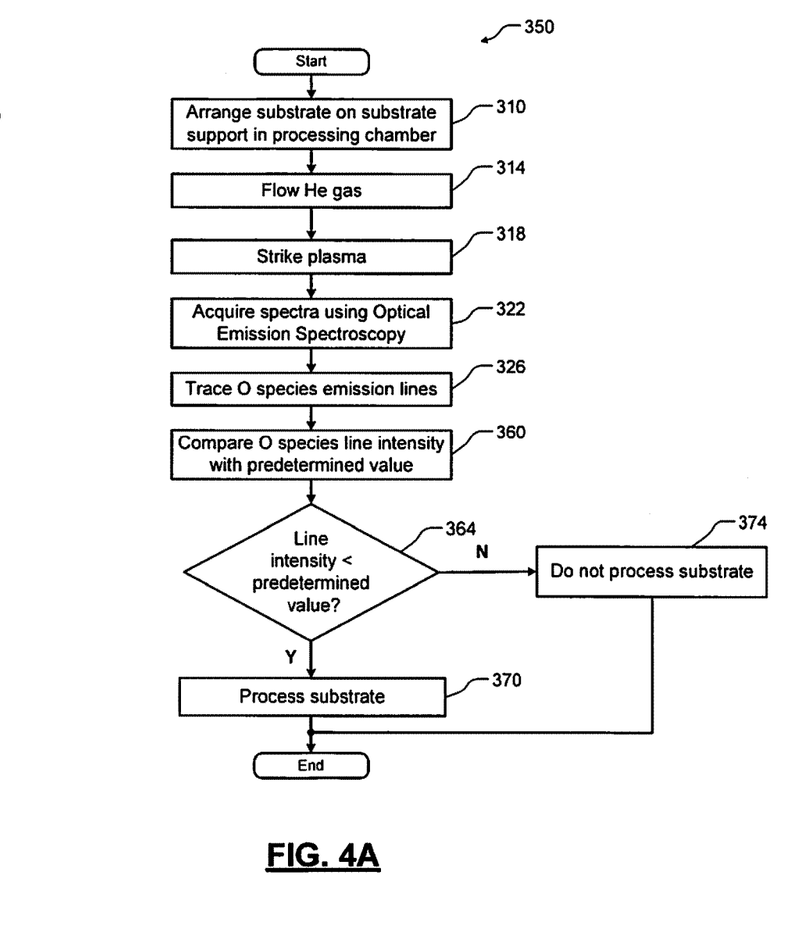

Referring now to FIG. 4A, a method 350 includes steps 310 to 326 described above. After 326, the method compares oxygen emission line intensity values with predetermined values at 360. At 364, the method determines whether the oxygen emission line intensity is less than the predetermined value. If 364 is true, the oxidation levels are sufficiently low and the substrate is processed at 370. If 364 is false, the oxidation levels are too high and the substrate is not processed at 374.

In some examples, the process proceeds when the measured oxidation level is greater than the predetermined level and does not proceed when the measured oxidation level is less than the predetermined level.

Figure 4B:
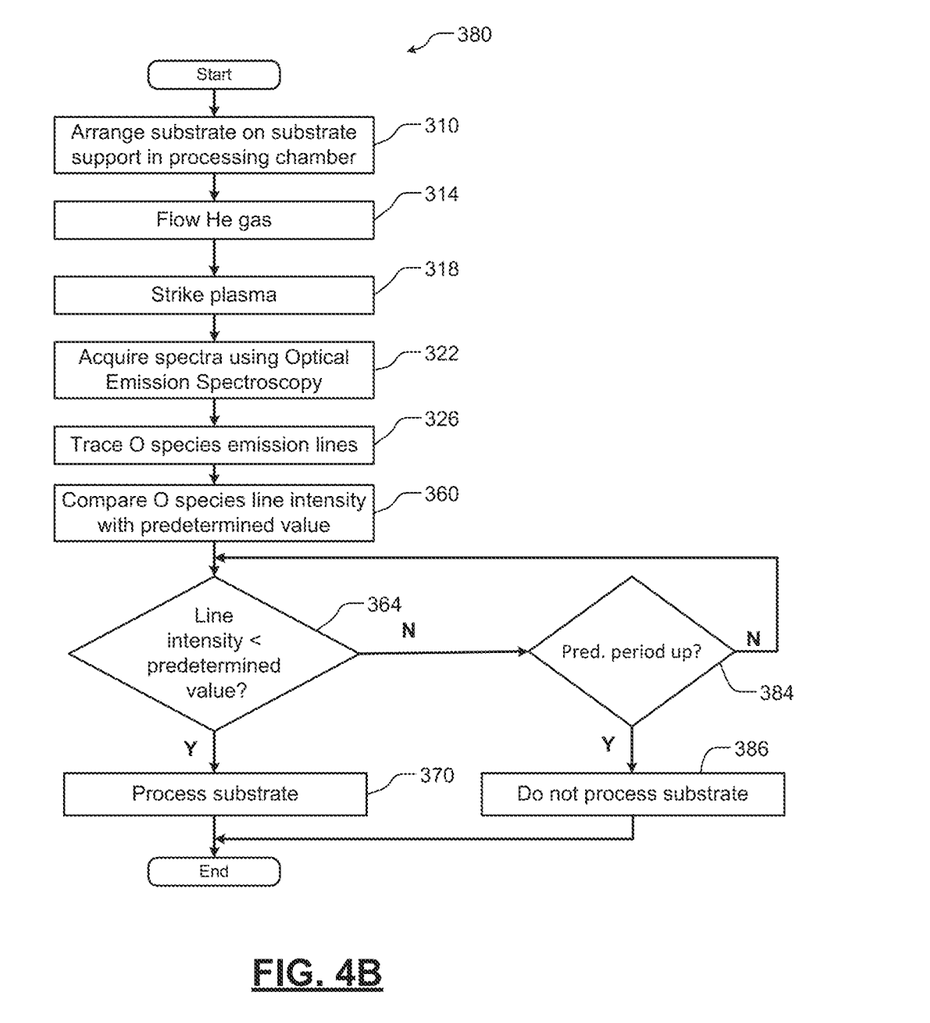

Referring now to FIG. 4B, a method 380 is shown that is similar to the method 350 in FIG. 4A. In the method 380, the substrate is processed as soon as the line intensity falls below the predetermined value. Otherwise, the method 380 will keep comparing the line intensity to the predetermined value for a predetermined period before determining that the substrate cannot be processed. If 364 is false (the line intensity is not less that the predetermined value), the method 380 continues with 384 and determines whether a predetermined period is up. If 384 is false, the method returns to 364. If 384 is true, the method continues with 386, does not process the substrate and the method 380 ends.

Figure 5:
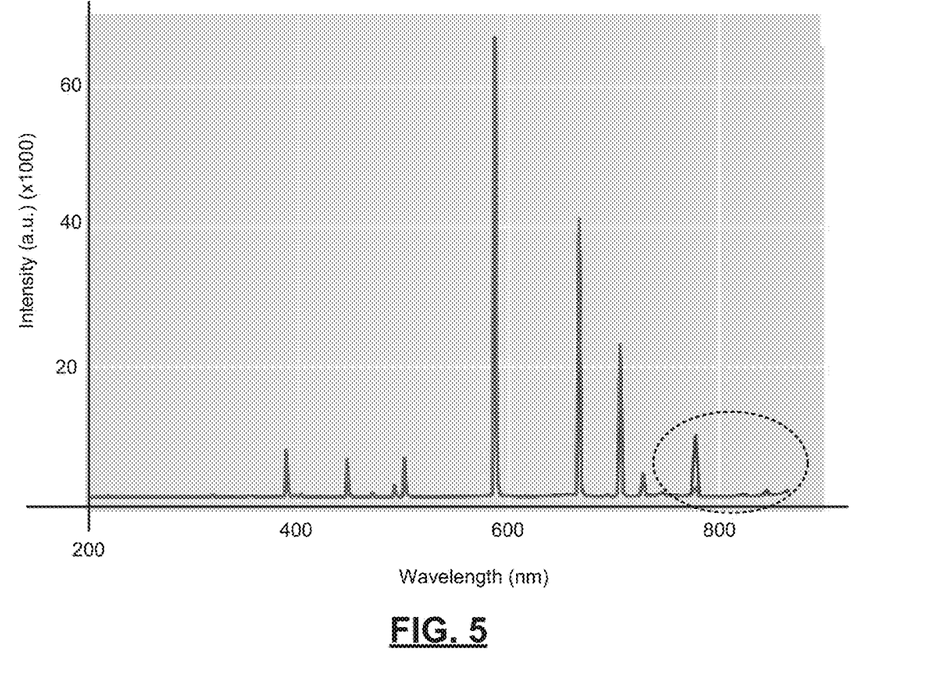
FIG. 5 is a graph illustrating an example of measured spectral intensity at various wavelengths.
Figure 6:
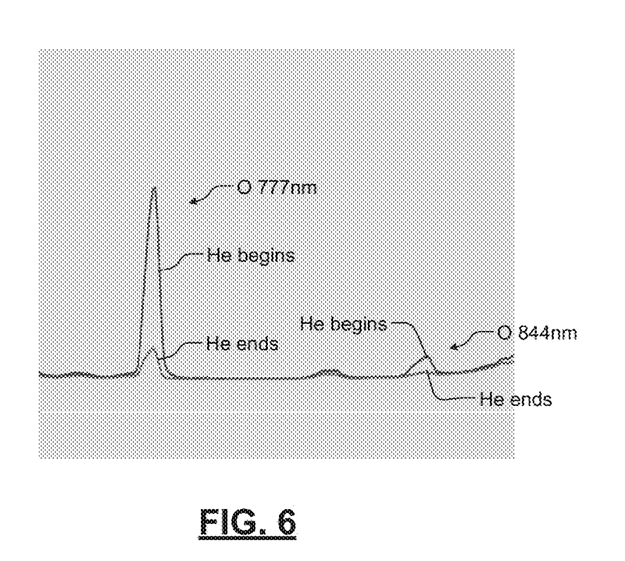
FIG. 6 is an enlarged graph illustrating a portion of FIG. 5.

Referring now to FIGS. 5-6, oxygen O peak intensity can be enhanced using He plasma. Peaks are detected at 777 nm and 844 nm, which is distinctly different than native peaks from He plasma emission lines. The characteristic emission line of O at 777 nm is at least 15 nm apart from He emission lines, which is well within typical OES resolution limits. In some examples, the 777 nm peak intensity decay is correlated with RGA $O_2$ (Mass 32) signal decay.

Referring now to FIG. 7, the 777 nm emission intensity is enhanced with He plasma. The O emission intensity is significantly higher (e.g. 4 times) than oxygen-based plasma alone. The measured signal intensity comparing to S/N ratio enables the method to detect over 6 decades of O concentration difference. OES signal intensity decay of O species can be correlated with measurements made by the RGA connected to chamber foreline as shown in FIG. 7.

Figure 8:
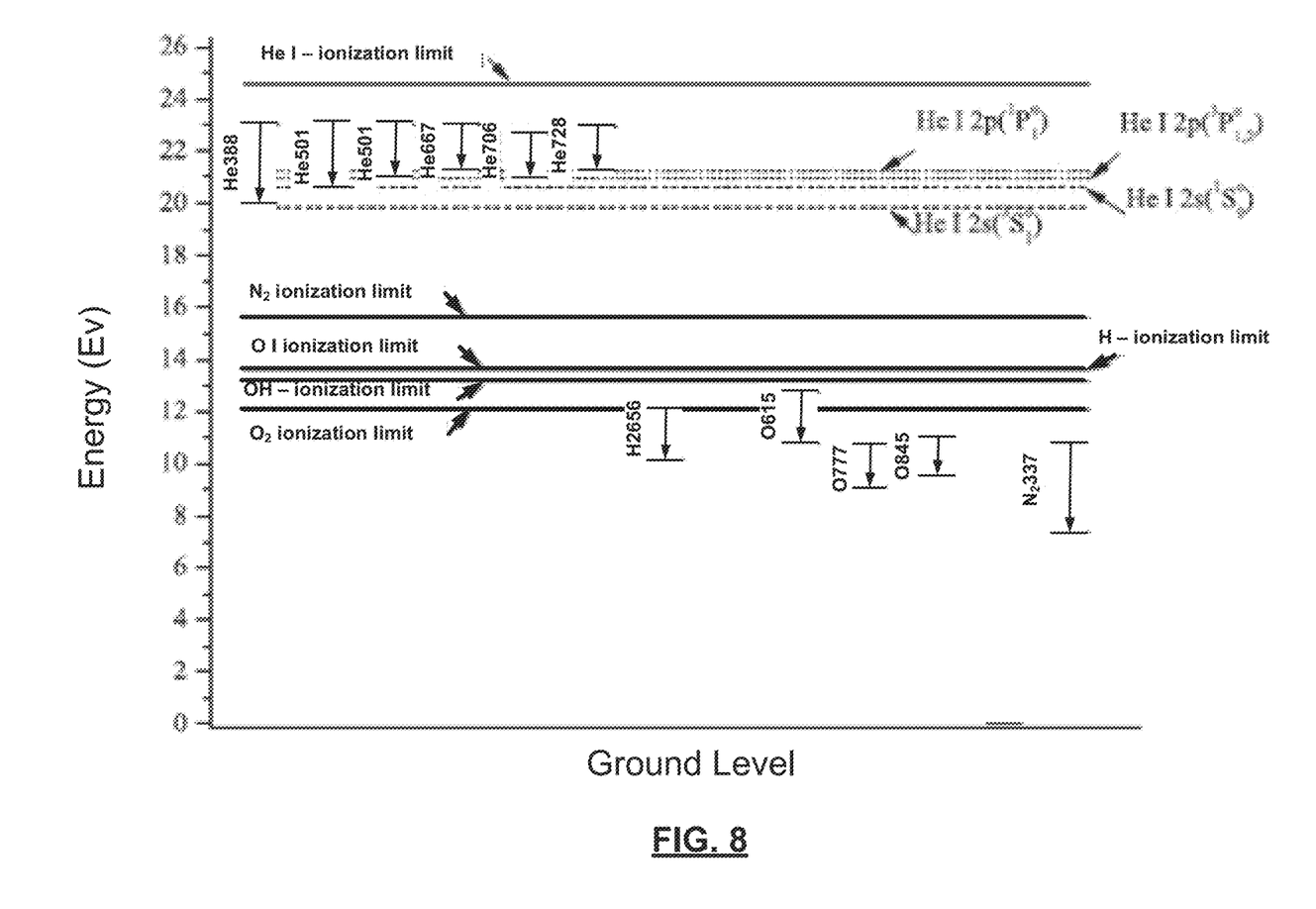
FIG. 8 is a graph illustrating an example of an energy diagram for helium and oxygen optical emission.

Referring now to FIG. 8, the detection systems and methods leverage high energy He metastable species that are excited by the ICP plasma source and that diffuse through the showerhead. The He metastable species have an energy level between 20-23 ev, which can activate the $O_2$ species in the area above the substrate. $O_2$ ionization limit is between 12-14 eV. In some examples, the OES viewport is arranged and oriented parallel to substrate surface, which enables detection of $O_2$ trace amounts above the substrate.

In addition to detecting oxygen species, the detection systems and methods can be used to detect other neutral gas species assuming that the He metastable atom energy is sufficient for excitation or ionization. For example, the detection systems and methods can be used to detect nitrogen $N_2$, which has ionization energy of about 15.4 eV versus the 20-23 eV ionization energy of the He metastable atom. While the same plasma source can be used for the preceding plasma process and the determination of $O_2$ levels near the substrate, a separate plasma source can be used to generate the He plasma to inject metastable He atoms into a region near the substrate. Furthermore, while He is disclosed, other gases having higher ionization energy for the corresponding metastable atoms than the neutral gas species to be detected can be used.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In some implementations, a controller is part of a system, which may be part of the above-described examples. Such systems can comprise semiconductor processing equipment, including a processing tool or tools, chamber or chambers, a platform or platforms for processing, and/or specific processing components (a substrate pedestal, a gas flow system, etc.). These systems may be integrated with electronics for controlling their operation before, during, and after processing of a semiconductor substrate or substrate. The electronics may be referred to as the "controller," which may control various components or subparts of the system or systems. The controller, depending on the processing requirements and/or the type of system, may be programmed to control any of the processes disclosed herein, including the delivery of processing gases, temperature settings (e.g., heating and/or cooling), pressure settings, vacuum settings, power settings, radio frequency (RF) generator settings, RF matching circuit settings, frequency settings, flow rate settings, fluid delivery settings, positional and operation settings, substrate transfers into and out of a tool and other transfer tools and/or load locks connected to or interfaced with a specific system.

Broadly speaking, the controller may be defined as electronics having various integrated circuits, logic, memory, and/or software that receive instructions, issue instructions, control operation, enable cleaning operations, enable endpoint measurements, and the like. The integrated circuits may include chips in the form of firmware that store program instructions, digital signal processors (DSPs), chips defined as application specific integrated circuits (ASICs), and/or one or more microprocessors, or microcontrollers that execute program instructions (e.g., software). Program instructions may be instructions communicated to the controller in the form of various individual settings (or program files), defining operational parameters for carrying out a particular process on or for a semiconductor substrate or to a system. The operational parameters may, in some embodiments, be part of a recipe defined by process engineers to accomplish one or more processing steps during the fabrication of one or more layers, materials, metals, oxides, silicon, silicon dioxide, surfaces, circuits, and/or dies of a substrate.

The controller, in some implementations, may be a part of or coupled to a computer that is integrated with the system, coupled to the system, otherwise networked to the system, or a combination thereof. For example, the controller may be in the "cloud" or all or a part of a fab host computer system, which can allow for remote access of the substrate processing. The computer may enable remote access to the system to monitor current progress of fabrication operations, examine a history of past fabrication operations, examine trends or performance metrics from a plurality of fabrication operations, to change parameters of current processing, to set processing steps to follow a current processing, or to start a new process. In some examples, a remote computer (e.g. a server) can provide process recipes to a system over a network, which may include a local network or the Internet. The remote computer may include a user interface that enables entry or programming of parameters and/or settings, which are then communicated to the system from the remote computer. In some examples, the controller receives instructions in the form of data, which specify parameters for each of the processing steps to be performed during one or more operations. It should be understood that the parameters may be specific to the type of process to be performed and the type of tool that the controller is configured to interface with or control. Thus as described above, the controller may be distributed, such as by comprising one or more discrete controllers that are networked together and working towards a common purpose, such as the processes and controls described herein. An example of a distributed controller for such purposes would be one or more integrated circuits on a chamber in communication with one or more integrated circuits located remotely (such as at the platform level or as part of a remote computer) that combine to control a process on the chamber.

Without limitation, example systems may include a plasma etch chamber or module, a deposition chamber or module, a spin-rinse chamber or module, a metal plating chamber or module, a clean chamber or module, a bevel edge etch chamber or module, a physical vapor deposition (PVD) chamber or module, a chemical vapor deposition (CVD) chamber or module, an atomic layer deposition (ALD) chamber or module, an atomic layer etch (ALE) chamber or module, an ion implantation chamber or module, a track chamber or module, and any other semiconductor processing systems that may be associated or used in the fabrication and/or manufacturing of semiconductor substrates.

As noted above, depending on the process step or steps to be performed by the tool, the controller might communicate with one or more of other tool circuits or modules, other tool components, cluster tools, other tool interfaces, adjacent tools, neighboring tools, tools located throughout a factory, a main computer, another controller, or tools used in material transport that bring containers of substrates to and from tool locations and/or load ports in a semiconductor manufacturing factory.

What is claimed is:

1. A measurement system to measure a concentration of neutral gas species above a substrate, comprising:
    a chamber;
    a substrate support located in the chamber to support a substrate;
    a plasma source to generate plasma in the chamber above the substrate, wherein the plasma generates metastable species having higher ionization energy than a neutral gas species, and wherein the metastable species excite the neutral gas species located above the substrate;
    an optical emission spectrometer (OES) sensor to measure spectra from a location above the substrate while the plasma is generated by the plasma source; and
    a controller configured to determine a concentration of the neutral gas species in a region above the substrate based on the measured spectra.

2. The measurement system of claim 1, wherein the controller is configured to selectively perform a process on the substrate based on the concentration.

3. The measurement system of claim 1, wherein the controller determines the concentration of the neutral gas species by comparing an intensity of the measured spectra at a predetermined wavelength to a predetermined reference.

4. The measurement system of claim 1, wherein the controller determines the concentration of the neutral gas species using a lookup table that is indexed by an intensity of the measured spectra at a predetermined wavelength.

5. The measurement system of claim 1, wherein the controller determines the concentration of the neutral gas species using a predetermined function and an intensity of the measured spectra at a predetermined wavelength.

6. The measurement system of claim 1, wherein the plasma source generates the plasma using a plasma gas mixture that does not include the neutral gas species.

7. The measurement system of claim 1, wherein a plasma gas mixture supplied to the plasma source includes helium and wherein the metastable species includes helium metastable species.

8. The measurement system of claim 7, wherein the plasma gas mixture further includes at least one gas selected from a group consisting of argon, neon and molecular nitrogen.

9. The measurement system of claim 7, wherein the neutral gas species includes oxygen species, and wherein the helium metastable species enhance characteristic emission spectra of the oxygen species at at least one of 777 nm and 844 nm.

10. The measurement system of claim 1, wherein the neutral gas species includes molecular oxygen.

11. The measurement system of claim 1, wherein the neutral gas species includes molecular nitrogen.

12. The measurement system of claim 1, wherein the OES sensor measures spectra travelling parallel to a plane including the substrate.

13. The measurement system of claim 1, wherein the chamber includes a viewport and further comprising a collimator tube arranged between the viewport and the OES sensor to collimate the spectra.

14. The measurement system of claim 13, wherein the collimator tube has an aspect ratio that is greater than 5:1.

15. A method for measuring a concentration of neutral gas species above a substrate, comprising:
    arranging a substrate on a substrate support in a chamber;
    generating plasma in the chamber above the substrate, wherein the plasma generates metastable species having higher ionization energy than a neutral gas species, wherein the metastable species excites the neutral gas species located above the substrate;
    measuring spectra from a location above the substrate using an optical emission spectrometer (OES) sensor while the plasma is present; and
    determining a concentration of the neutral gas species in a region above the substrate based on the measured spectra.

16. The method of claim 15, further comprising selectively performing a process on the substrate based on the concentration.

17. The method of claim 15, wherein determining the concentration of the neutral gas species includes comparing an intensity of the measured spectra at a predetermined wavelength to a predetermined reference.

18. The method of claim 15, wherein determining the concentration of the neutral gas species includes using a lookup table that is indexed by an intensity of the measured spectra at a predetermined wavelength.

19. The method of claim 15, wherein determining the concentration of the neutral gas species includes using a predetermined function and an intensity of the measured spectra at a predetermined wavelength.

20. The method of claim 15, further comprising supplying a plasma gas mixture that does not include the neutral gas species.

21. The method of claim 15, further comprising supplying a plasma gas mixture including helium, wherein the metastable species includes helium metastable species.

22. The method of claim 21, wherein the neutral gas species includes molecular oxygen species, and wherein the helium metastable species enhance characteristic emission spectra of the oxygen species at at least one of 777 nm and 844 nm.

23. The method of claim 21, wherein the plasma gas mixture further includes at least one gas selected from a group consisting of argon, neon and molecular nitrogen.

24. The method of claim 15, wherein the neutral gas species includes molecular oxygen.

25. The method of claim 15, wherein the neutral gas species includes molecular nitrogen.

26. The method of claim 15, further comprising measuring spectra travelling parallel to a plane including the substrate.

27. The method of claim 15, further comprising providing a viewport and arranging a collimator tube between the viewport and the OES sensor to collimate the spectra that is received by the OES sensor.

28. The method of claim 27, wherein the collimator tube has an aspect ratio that is greater than or equal to 5:1.

* * * * *